(12) United States Patent
Nistri et al.

(10) Patent No.: US 7,030,081 B2
(45) Date of Patent: Apr. 18, 2006

(54) MUTEINS OF THE CGRP 1-7 PEPTIDE FRAGMENT AND USE THEREOF AS NICOTINIC NEURONAL RECEPTOR ENHANCERS

(75) Inventors: Andrea Nistri, Romans (IT); Silvia Di Angelantonio, Rome (IT)

(73) Assignee: S.I.S.S.A.- Scuola Internazionale Superiore di Studi Avanzati, (IT)

( * ) Notice: Subject to any disclaimer, the term of this patent is extended or adjusted under 35 U.S.C. 154(b) by 38 days.

(21) Appl. No.: 10/373,982

(22) Filed: Feb. 25, 2003

(65) Prior Publication Data

US 2003/0220235 A1 Nov. 27, 2003

Related U.S. Application Data

(63) Continuation of application No. PCT/IT01/00477, filed on Sep. 13, 2001.

(30) Foreign Application Priority Data

Sep. 15, 2000 (IT) .......................... RM2000A0500

(51) Int. Cl.
*C07K 5/00* (2006.01)
*C07K 7/00* (2006.01)
(52) U.S. Cl. .......................... 514/2; 530/307; 530/329; 530/330
(58) Field of Classification Search ............... 500/307, 500/329, 330; 514/2
See application file for complete search history.

(56) References Cited

OTHER PUBLICATIONS

Mimeault et al. (1993), Eur. J. Biochem. 213(3): 927-934.*
Di Angelantonio et al. (2002), Mol. Pharmacol. 61(1): 43-54.*
Nistri et al. (2002), Ann. N. Y. Acad. Sci. 971: 100-107.*
Katsuya et al., "Calcium-dependent enhancing effect by calcitonin gene-related peptide on muscle nicotinic receptor desensitization", Japanese Journal of Pharmacology, vol. 79, No. suppl. 1 (1998).
Giniatullin et al., "Calcitonin gene-related peptide rapidly downregulates nicotinic receptor function and slowly raises intracellular Ca2+ in rat chromaffin in vitro", J. of Neuroscience vol. 19, No. 8, p. 2945-53, (1999).
Trevor et al., "Structure-activity profile of calcitonin gene-related peptide in peripheral and brain tissues evidence for receptor multiplicity", J. of Pharmacology & Experimental Therapeutics, vol. 251, No. 2, p 718-25, (1989).

* cited by examiner

*Primary Examiner*—Robert S. Landsman
*Assistant Examiner*—Jon M Lockard
(74) *Attorney, Agent, or Firm*—Gauthier & Connors LLP

(57) ABSTRACT

Muteins of the Ser-Cys-Asn-Thr-Ala-Thr-Cys sequence from the N-terminal 1-7 fragment of the CGRP peptide, possessing an enhancing action on the activation of neuronal nicotinic receptors, their pharmaceutical compositions containing the same and their use for the potential therapy of neurological diseases are described.

3 Claims, 7 Drawing Sheets

CGRP1-7: Ser-Cys-Asn-Thr-Ala-Thr-Cys     SEQ ID No. 1

Figure 1:

CGRP1-6: Ser-Cys-Asn-Thr-Ala-Thr     Residues 1-6 of SEQ ID No. 1

CGRP1-5: Ser-Cys-Asn-Thr-Ala     Residues 1-5 of SEQ ID No. 1

CGRP1-4: Ser-Cys-Asn-Thr     Residues 1-4 of SEQ ID No. 1

CGRP1-3: Ser-Cys-Asn     Residues 1-3 of SEQ ID No. 1

SEQUENCE LISTING

```
<160> NUMBER OF SEQ ID NOS: 2

<210> SEQ ID NO 1
<211> LENGTH: 7
<212> TYPE: PRT
<213> ORGANISM: Homo sapiens

<400> SEQUENCE: 1

Ser Cys Asn Thr Ala Thr Cys
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: mutein

<400> SEQUENCE: 2

Ser Cys Asn Thr Ala Thr Ala
1               5
```

MUTEINS OF THE CGRP 1-7 PEPTIDE FRAGMENT AND USE THEREOF AS NICOTINIC NEURONAL RECEPTOR ENHANCERS

PRIORITY INFORMATION

This application claims priority to International Patent Application No. PCT/IT01/00477, filed Sep. 13, 2001 and Application No. RM2000A000500, filed Sep. 15, 2000.

The present invention relates to muteins of the CGRP 1-7 peptide fragment (Calcitonin Gene Related Peptide) and use thereof as neuronal nicotinic receptor enhancers. In particular, the invention relates to muteins of the N-terminal CGRP 1-7 peptide fragment of the whole 37 amino acid peptide, having at least 4 amino acids, and use thereof for the preparation of potential drugs for the treatment of neurological diseases associated with functional deficit of the neuronal nicotinic receptors.

Nicotinic receptors are key molecules for cholinergic transmission to the neuromuscular junction of striated muscles (muscle-type nicotinic receptors), peripheral ganglion synapses of the autonomic nervous system and in several brain areas (neuronal nicotinic receptors) (Gotti et al., Paterson and Nordberg, 2000).

All nicotinic receptors are a pentameric sub-unit aggregate forming a structure (inserted within the cellular membrane) which contains a central channel. Nicotinic receptors are made up by various sub-unit combinations and, depending on such combinations, they show different functional and pharmacological properties.

The sub-units are named as below: α sub-units (α1–α9), i.e. sub-units which bind agonists and contain disulfide bridges between contiguous cysteine residues, exemplified by Cys-192-Cys 193 in the muscular α1 sub-unit. Non-α sub-units, which confer particular properties to the receptors, do not contain cysteine residues and, depending on their amino acid sequence, are named β1–β4, γ, ε, δ. All sub-units have a similar topographic structure including one extended extracellular domain (N-terminal), four transmembrane domains (M1–M4), one intracellular domain (whose length depends on the sub-unit) which joins M3 and M4 domains and one small extracellular C-terminal domain (Changeux and Edelestein, 1998).

The amino acid sequence analysis of various sub-units shows that nicotinic receptors can be divided into three sub-classes. The first family includes muscle-type heteromeric receptors, typically found in skeletal muscle and fish electrical organs, with $(\alpha 1)_2 \beta 1 \gamma \delta$ and $(\alpha 1)_2 \beta 1 \gamma \epsilon$ pentameric structures in fetal or adult form, respectively. These muscular receptors are selectively blocked by α-bungarotoxin.

The second family includes neuronal nicotinic receptors (nAChR) consisting of α-bungarotoxin-insensitive, heteromeric sub-units. Also these receptors have a pentameric structure resulting from various combinations of α2, α3, α4 and α6 with β2 or β4 and in some cases also with α5 or β3 sub-units.

The third family includes α-bungarotoxin-binding nicotinic neuronal homomeric receptors consisting of 5 identical sub-units (α7, α8 or α9).

The binding site of acetylcholine and other agonists is located on the N-terminal extracellular domain at the boundary between α and non-α sub-units. In heteromeric neuronal receptors the α and β sub-units contribute to the binding site.

Studies about the structure, functions and pharmacology of neuronal receptors are very important because it was recently shown that these receptors are involved in a large number of cerebral functions and pathological mechanisms of nervous system diseases (for recent reviews see Clementi and Adlkofer Special Issue on "nicotinic neuronal receptors" 2000).

Thus, it follows that agonists, antagonists and modulators of these receptors have stimulated widespread therapeutic or diagnostic interest in relation to different neuropathological conditions.

Some of the pathologies resulting from dysfunction of neuronal nicotinic receptors are, for example, Alzheimer's disease, Parkinson's disease, epilepsy, other mental diseases such as schizophrenia, Tourette's syndrome, anxiety and depression.

Alzheimer's Disease

Alzheimer's disease (AD) is a progressive neurodegenerative condition affecting ¹⁄₁₀ of the over 65 y old individuals. It determines more than 50% of senile dementias (and the majority of the pre-senile dementias) and it is characterized by a gradual deterioration of higher cognitive functions, including memory. The brains of AD patients, inspected post-mortem, show two neuropathological characteristics representing the two principal indicators for the AD diagnosis: intracellular deposits of neurofilaments and extracellular plaques.

AD brains show severe loss of cholinergic innervation within the cerebral cortex and hippocampus (Coyle et al., 1983). This results in the hypothesis that the cognitive deterioration is strictly related to degeneration of the cholinergic pathways (cholinergic hypothesis; Bartus et al., 1982).

Furthermore, in AD brains, nicotinic agonist binding is remarkably reduced with respect to controls. In these brains, however, α-bungarotoxin binding is not reduced, indicating that apparently no loss of homomeric α7 receptors occurs. Studies carried out on AD affected brains have shown the α4β2 to be the most damaged receptor class (Warpman and Nordberg, 1995).

The commonest treatment for AD aims at restoring decreased cholinergic transmission. Usually such an approach relies on cholinesterase inhibitors, such as tacrine, donezepil and rivastigmine, which avoid degradation of acetylcholine released from cholinergic neurons, and therefore increase the acetylcholine concentration available for interaction with nAChRs. This class of drugs provides only a palliative effect on AD symptoms while it is questionable their ability to slow down the neurodegeneration (Amberla et al., Maltby et al. 1994, Nordberg et al. 1998, Nordberg and Svensson 1998). It is likely that any potential benefit of these drugs originates from nAChRs activation both via increased neurotransmitter extracellular concentration and via allosteric nAChR modulation carried out by tacrine or galantamine (Maelicke et al., 1995, Nordberg and Svensson 1998).

Several studies suggest activation of nAChRs to be important for AD therapy:

1) nAChR activation by nicotine increases memory function. In animal models it was observed that β2 sub-unit lacking mice show learning memory deficits (Picciotto et al. 1995) and that healthy animals, chronically treated with nicotine, show better memory (Levin 1992). Nicotine increases memory in AD patients as well (Rusted et al. 1994).
2) Nicotinic receptor activation facilitates release of many brain neurotransmitters like acetylcholine, dopamine, GABA and glutamate (Wonnacott 1997).
3) nAChR activation partially protects against β-amyloid toxicity. In fact, nicotine prevents β-amyloid induced cell death of cultured neurons, an effect blocked by dihydro-β-erythroidine, which is an α4β2 receptor antagonist. Also cytisine, another nicotinic agonist, inhibits β-amyloid toxicity (Kihara et al. 1998).

Hence, nicotinic neuronal receptor activation is an important therapeutic object but, up to now, it is hardly achievable and not fully understood with respect to its implications for long term receptor function (Sjoberg et al 1998, Perry et al. 2000).

Parkinson's Disease

In analogy with AD, Parkinson's disease also shows loss of cholinergic neurons in the basal ganglia, together with strong reduction in high affinity nicotine-binding sites (Whitehouse et al. 1983, Lange et al. 1993). In addition to motor dysfunction, PD patients often show cognitive deficits associated with nAChR loss (Perry et al. 1995). The most important environmental factor in PD patients is that this pathology is less frequent in smokers (Morens et al 1995). Although tobacco contains numerous substances in addition to nicotine, the latter is the most probable candidate for such an effect. For example, in rodents chronic treatment with nicotine prevents degeneration of dopaminergic neurons, a pathophysiological hallmark of PD (Janson and Moller 1993). In mice nicotine is partially neuroprotective against the basal ganglia lesions induced experimentally induced by the drug MPTP. Furthermore, the new, specific α4β2 receptor agonist, SIB-1508Y, when administered in combination with L-DOPA, increases the cognitive capacities in monkeys with experimental PD (Schneider et al. 1998a, 1998b).

Epilepsy

Epilepsy includes an heterogeneous group of central nervous system disorders. Among these, autosomal frontal lobe epilepsy (ADNFLE) is a partial epilepsy causing short lasting convulsions during sleep. It was recently demonstrated that ADNFLE results from a mutation of the gene encoding for the nAChR α4 sub-unit. This mutation consists of the replacement of a phenylalanine for serine (Ser247) in the M2 transmembrane domain (Steinlein et al 1995). This mutation modifies the properties of the α4β2 channels expressed in frog oocytes. A second mutation, again at the level the α4 sub-unit, was found in another family affected by the same epilepsy syndrome. This mutation consists of the insertion of a leucine into the C-terminal at position 259 (extracellular) in the M2 domain (Steinlein et al. 1995). Although the latter mutations is better tolerated clinically, both mutations reduce the calcium permeability of the α4β2 receptors (Weiland et al. 1996).

Furthermore the serine 247 mutated receptors show an ACh affinity 7 times smaller than normal receptors and desensitize more readily (Bertrand et al. 1998).

Since epilepsy is thought to originate from excessive activation of brain neurons, it seems contradictory that reduced function of nicotinic receptors can produce convulsions. The explanation possibly stems from the fact that α4β2 receptors possess a pre-synaptic action to modulate release of inhibiting neurotransmitters such as GABA and glycine (Wonnacott 1997). Higher release of GABA and glycine from inhibitory neurons, or activation of these same neurons mediated by α4β2 receptors, could prevent epileptic seizures.

For these reasons, drugs which can enhance directly this class of nicotinic receptors could be useful for the treatment of this form of epilepsy.

Other Mental Disorders

In addition to these neuropathologies, schizophrenia has also been suggested to be related to abnormal nAChR activation because in the brain of the schizophrenics there is a significant reduction in α7 receptors in the hippocampus CA3 region and in the frontal cortex (Freedman et al. 1995, 1997). Likewise, for the therapy of the Tourette's syndrome the aim is to develop nAChR targeting drugs (Olale et al. 1997). Nicotinic receptors are apparently involved in the physiopathology of anxiety and depression (Decker et al. 1994, Maggio et al. 1998).

Furthermore, the role of the nicotinic receptors in tobacco dependence has been pointed out. The number of the nicotinic receptors increases following a prolonged exposition to nicotine. Post-mortem studies on smoker brains reveal an increase in nicotine and acetylcholine binding sites proportional to the number of smoked cigarettes (Benwell et al 1988, Breese et al 1997). In addition, the number of these binding sites is lower in the brains of ex-smokers than in non-smokers. The interpretation of this phenomenon is that nAChR desensitization and subsequent hyper-expression, resulting from chronic exposition to nicotine, are the basis of nicotine tolerance and dependence occurring in smokers (Dani and Heinemann 1996).

In view of above considerations, it is therefore apparent the need to identify and provide chemical substances for the therapy of diseases resulting from nAChR dysfunction. Ideally these substances should be able to enhance rapidly and persistently the responses mediated by the nAChR activation without desensitizating them. If these substances are able to act directly on the agonist binding sites (for acetylcholine or nicotine), there would be the additional advantage of highly specific action without affecting other receptor systems.

Up to date there are problems to study nAChRs in native systems because nAChRs are widely localized at post-synaptic as well at pre-synaptic level, within the main cholinergic pathways of central and peripheral nervous systems (Lindstrom, 1997).

Many studies have been carried out on heterologous expression systems, consisting of cells constitutively lacking nicotinic receptors and made to express nAChRs with various sub-unit combination. Different biophysical and pharmacological properties of numerous subunit aggregates can then be investigated.

Often, the first step is the use of *Xenopus oocytes* as expression system. This approach is, however, unsuitable to understand many aspects concerning the role and function of native receptors, probably because in amphibian cells, with half gene complement, produce post-translational modifications of nAChRs to alter their activity. For example, atropine and ivermectine, which modulate oocyte-expressed nAChRs, do not have a similar effect on native receptors (Krause et al. 1998).

The use of mammalian cells, e.g. HEK cells, as expression systems, presents also severe limitations because these are not neuronal cells and they lack the intracellular receptor modulation mechanisms typical of neurons.

Thus, native receptor-expressing cells remain indispensable for biophysical and pharmacological studies of nAChRs, particularly for the development of drugs active on central and peripheral neurons for the diagnosis and treatment of various nerupsychiatric disorders.

A suitable experimental model, used in the present invention, is represented by rat chromaffin cells which constitute the medullary portion of adrenal glands. These glands belong to the autonomic nervous system as chromaffin cells origin from the neural crest.

Chromaffin cells are exposed to acetylcholine released by the splanchnic nerve and possess high nAChR density. Due to their properties, these cells have been widely used for pharmacological and physiological studies aiming at characterizing nAChRs (Khirough et al., 1998, 1997, Giniatullin et al., 1999).

Muscle-type nicotinic receptors are known to be strongly modulated by the endogenously occurring CGRP neuropeptide which operates through activation of intracellular second messengers (Calcitonin Gene Related Peptide; Mulle et al., 1988; Miles et al., 1989; Lu et al., 1993). Our laboratory has recently reported CGRP to block nAChRs competitively, i.e. displacing the cholinergic agonist from its binding site on nAChRs (Giniatullin et al. 1989). It is noteworthy to point out that this effect is not mediated by conventional, G-proteins coupled, CGRP receptors and associated intracellular transduction systems (Giniatullin et al., 1999). By means of structure-action studies it was shown that the CGRP inhibiting activity is already completely present within the 1-7 N-terminal fragment (Giniatullin et al. 1999). Like native CGRP, CGRP 1-7 shows a rapidly developing, competitive antagonism readily reversible on wash (Giniatullin et al. 1999).

A novel and unexpected discovery, that is the subject of the present patent application, is that some fragments of the CGRP peptide (muteins) rapidly and reversibly enhance responses mediated by the activation of native neuronal nicotinic receptors. These receptors were studied in cultured chromaffin cells on which we also characterized their native receptor identity. The effects of peptide muteins was observed at sub-μM concentrations and depended on the concentration of the nicotinic agonist. In fact, while responses to maximal doses of the agonist were not enhanced, those to small doses were rapidly increased. In the absence of nAChR activation these compounds were inactive.

Furthermore, we observed that the peptide CGRP 1-6 did not modify the muscle-type nicotinic receptor responses, therefore indicating its selectivity for neuronal ones. These findings suggest that certain peptide derivatives shorter than CGRP 1-7 exert an unusual action involving an apparently competitive modulation of the agonist binding site. We also showed that the CGRP 1-6 fragment acted differently from typical allosteric modulators like physostigmine. Thus, CGRP 1-6 and its derivatives can be used as lead compounds for the potential treatment of symptoms of neurological diseases associated with functional deficits of nAChRs.

In addition, we observed that elimination of seventh amino acid from the CGRP 1-7 peptide, namely cysteine, removed the single disulfide bridge formed in this peptide, allowing it to assume a new spatial conformation.

Hence, the object of the present invention is a mutein derived from the CGRP 1-7 (Ser-Cys-Asn-Thr-Ala-Thr-Cys, SEQ ID No. 1) peptide and endowed with enhancing action on nAChRs.

Mutein means a peptide modified by substitution, modification or deletion of one or more amino acids, retaining its enhancing action.

Enhancer means a substance which does not show direct potentiating activity on receptors, but that increases receptor responses to agonists.

According to the present invention, one CGRP 1-7 peptide mutein can have a substitution, modification or deletion of the cysteine residue in position 7 so as the disulfide bridge with cysteine residue in position 2 cannot be formed.

The peptide in which cysteine is replaced by alanine has the following amino acid sequence:

Ser-Cys-Asn-Thr-Ala-Thr-Ala (SEQ ID No. 2) is termed CGRP 1-7 A and represents an example of CGRP 1-7 peptide mutein.

A CGRP peptide mutein has an amino acid sequence inclusive of at least 4 amino acids, i.e. Ser-Cys-Asn-Thr (residues 1–4 of SEQ ID No. 1); preferably, 5 amino acids, i.e. Ser-Cys-Asn-Thr-Ala (residues 1–5 of SEQ ID No. 1); even more favourably, 6 amino acids, i.e. Ser-Cys-Asn-Thr-Ala-Thr (residues 1–6 of SEQ ID No. 1).

It is further object of the invention a pharmaceutical composition comprising at least one CGRP peptide mutein and one or more pharmaceutically acceptable co-adjuvants and excipients.

The pharmaceutical composition can further include one or more nAChR allosteric modulators like, for example, physostigmine.

The mutein according to this invention can be used as drug, for example for the symptomatic treatment of neurological diseases associated with functional deficit of nicotinic neuronal receptors, for example, Alzheimer's disease, Parkinson's disease, epilepsy, psychiatric diseases.

The present invention now will be described by means of representative (but not limiting) examples of the principal achievements with particular reference to the enclosed illustrations:

FIG. 1 shows the amino acid sequences of the terminal CGRP fragment. CGRP 1-7 includes a disulfide bridge between the two cysteines at positions 2 and 7, respectively.

Figure 2:
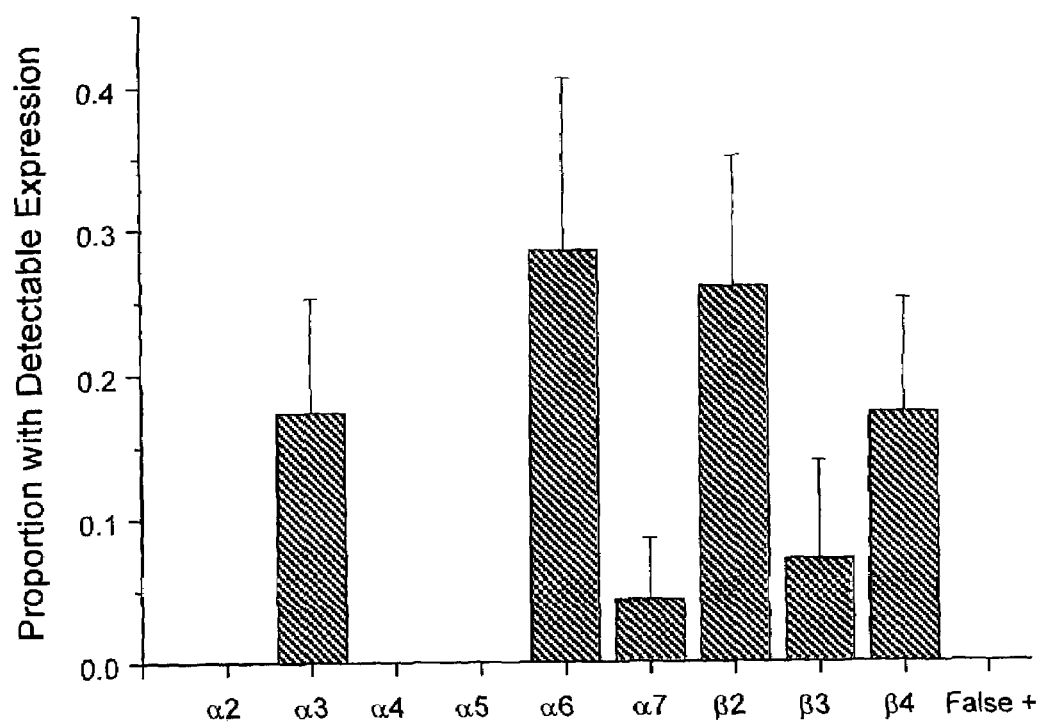

FIG. 2 reports the results of RT-PCR analysis performed on single chromaffin cells. mRNAs correspondent to the nicotinic sub-units expressed by chromaffin cells are represented by histograms showing their incidence on the normalized total (expressed as 1). The main sub-units found are $\alpha 3$, $\alpha 6$, $\beta 2$ and $\beta 4$.

Figure 3:
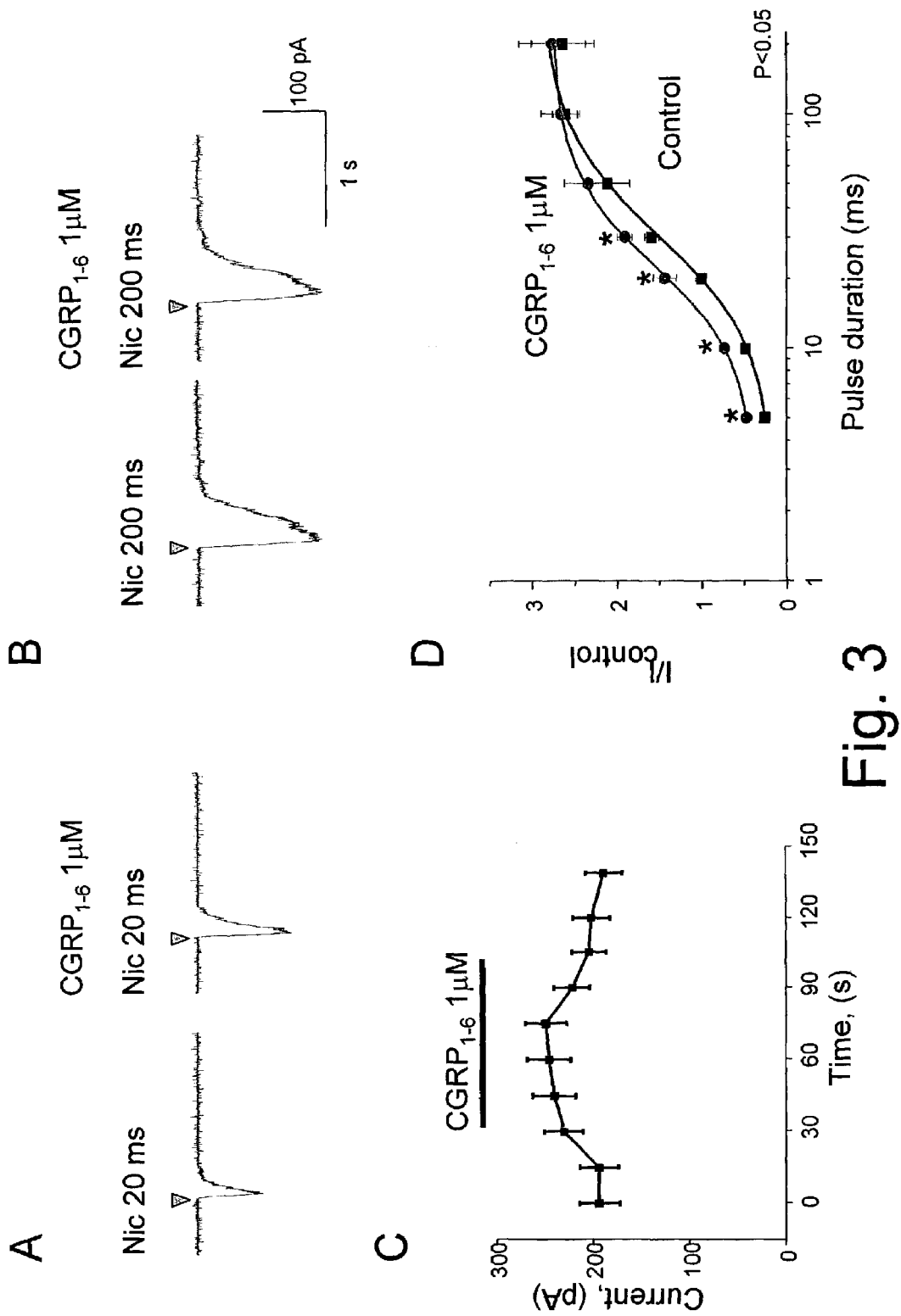

FIG. 3 shows the effect of CGRP 1-6 on nAChR-mediated ionic currents following activation by focal nicotine application. A: sub-maximal currents induced by a non-saturating nicotine pulse (20 ms) are enhanced by this peptide fragment, while the maximal currents are not modified (B). C: time profile of the CGRP 1-6 effect on nAChRs: the enhancement is rapidly induced and the current returns back to the initial value after 45–60 sec washout. D: dose (expressed as pulse duration; see Di Angelantonio and Nistri, 2001)/response (expressed as normalized ionic current, I) curve for nicotine in control solution and in the presence of CGRP 1-6. Note that the action of the peptide shifts the curve to left in a parallel fashion without maximum response modification (n=5–12 cells).

Figure 4:
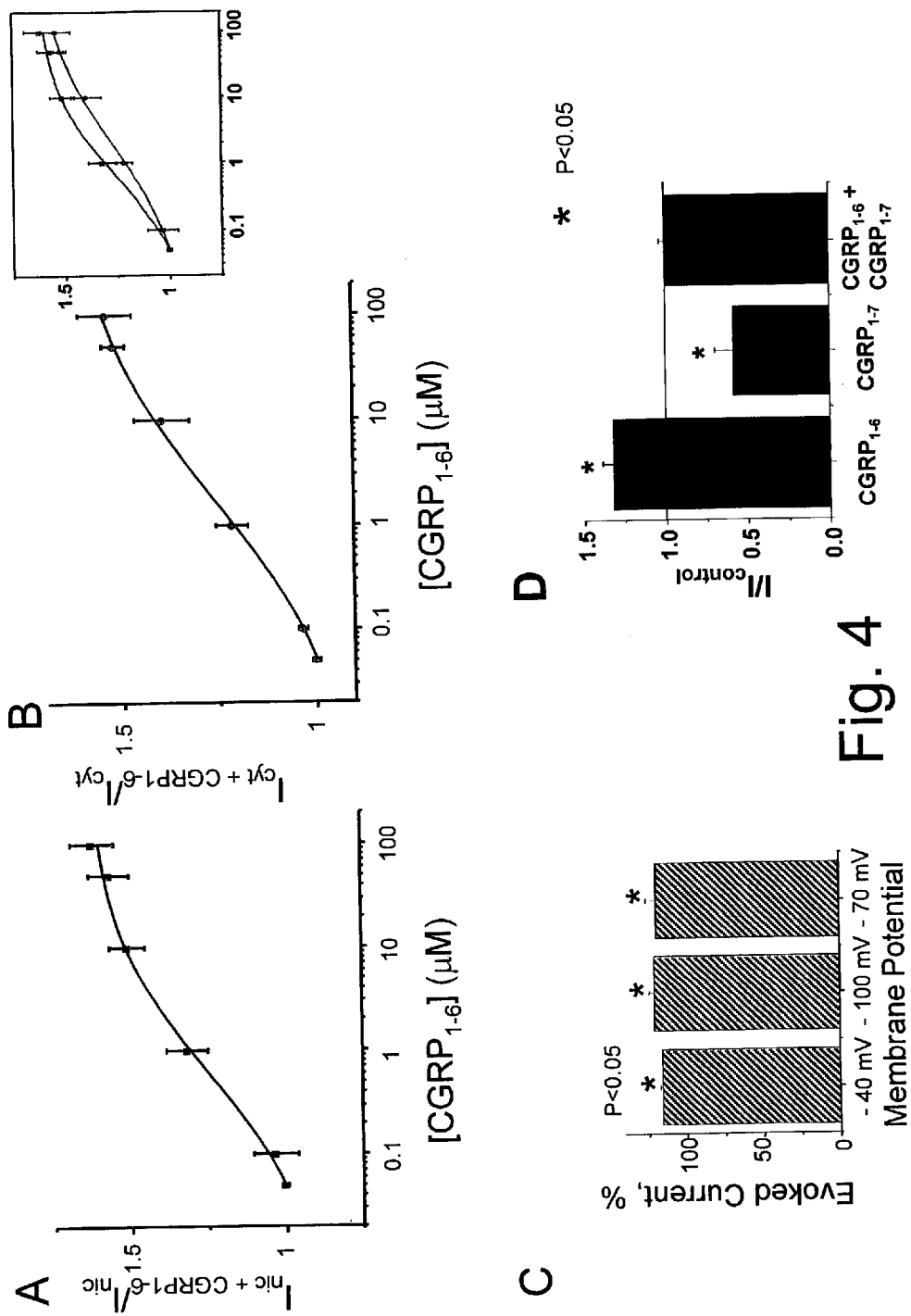

FIG. 4 demonstrates the mechanism of action of CGRP 1-6. A: the diagram shows the enhancement of nicotinic currents (0.1 mM, 20 ms) by different CGRP 1-6 concentrations; the enhancing action threshold is 0.1 μM. B: when cytisine (0,1 mM, 20 ms) is used as an agonist, the same potentiation is observed. Abscissa: CGRP 1-6 concentration (log units); ordinate: enhanced/control current ratio. The inset to the right of FIG. 4B shows superimposed plots for the enhancement by CGRP 1-6 of nicotine or cytisine currents: these graphs do not differ from each other, indicating that the enhancement does not depend on the choice of agonist. C: histograms demonstrating that the enhancing effect of nAChR mediated currents does not depend on the membrane potential (reported below each histogram as mV values correspondent to the clamp potential; n=7). D: comparison between the action of CGRP 1-6 and CGRP 1-7 on nAChRs: note that the CGRP 1-6 enhancing action counteracts the CGRP 1-7 competitive antagonism. All the responses are expressed as fractional, nicotine-induced currents in the presence of various drugs compared to control.

Figure 5:
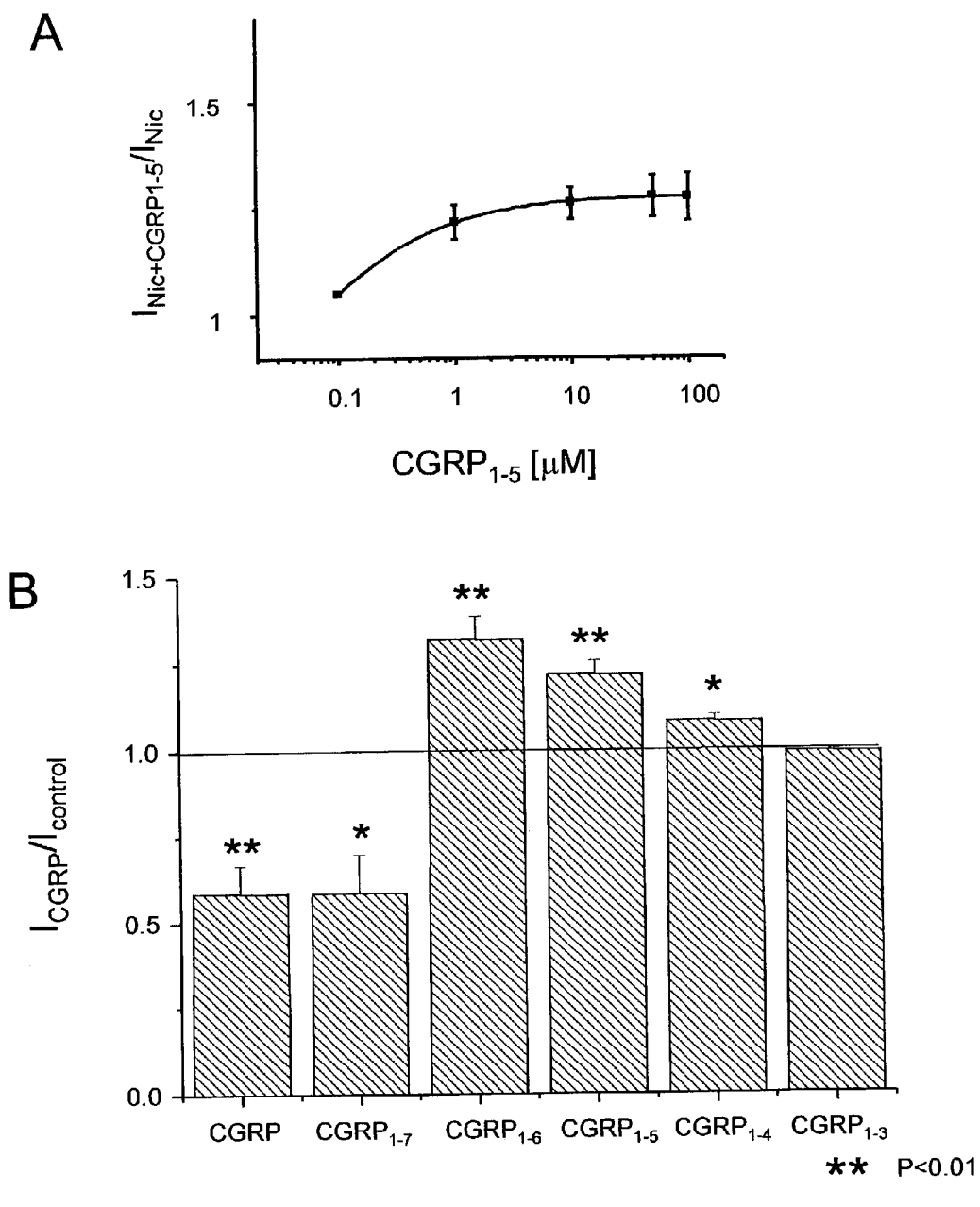

FIG. 5 shows the action of CGRP 1-5, 1-4, and 1-3 on nAChRs. A: the diagram shows that the CGRP 1-5 fragment enhances nAChR mediated currents; this effect is concentration-dependent but the ability by CGRP 1-5 to enhance receptor responses is lower than the one of fragment 1-6 (compare it with data in FIG. 4A). B: Summary histograms showing the action of various CGRP fragments on nicotinic currents. CGRP 1-4 possesses a modest enhancing effect while CGRP 1-3 is inactive. For comparison, data related to the nAChR antagonism induced by CGRP and its 1-7 fragment are also reported. All responses are expressed as ratio over control.

Figure 6:
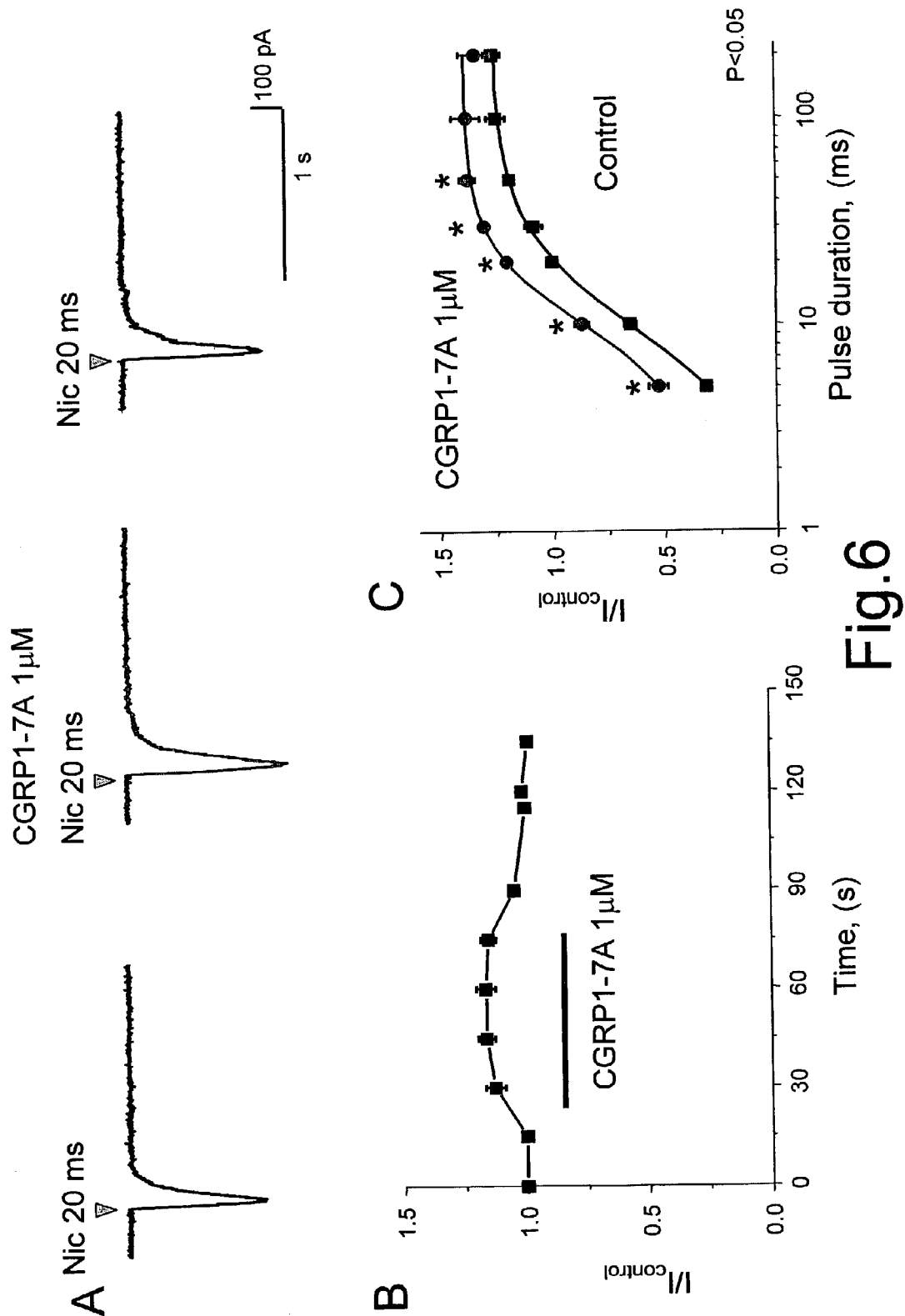

FIG. 6 shows the effect of the CGRP 1-7A fragment (Cys7 replaced with Ala) on nicotine induced responses. A: examples of currents induced by 20 ms nicotine and their enhancement by application of 1 µM CGRP 1-7 A. This effect disappears after peptide washout (right panel). B: time profile of the enhancement by CGRP 1-7 A of the responses to 20 ms nicotine exposure. Note rapid onset of the enhancement which reaches about 18% in few seconds and is easily reversible after wash. C: dose/response curves for nicotine (doses expressed as application length, ms) in control solution and in the presence of CGRP 1-7 A. This treatment shifts the curve to left in a parallel fashion without modification of the maximum response. Asterisks indicate data statistically different from control ($P<0.05$).

Figure 7:
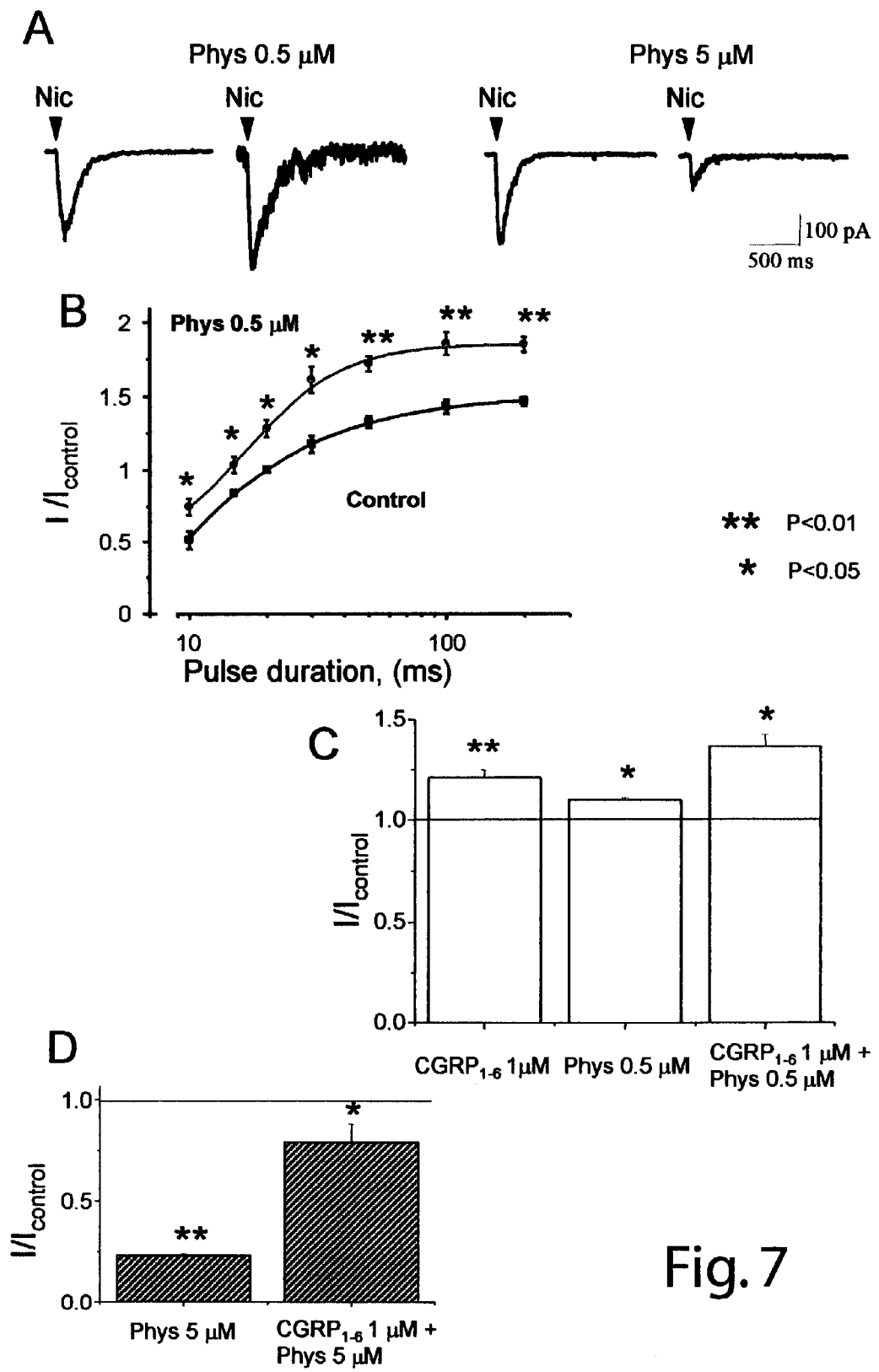

FIG. 7 presents studies on the potential interaction between the CGRP 1-6 fragment and physostigmine (Phys). Physostigmine is a nAChR allosteric modulator: the figure shows that, on the same cell, low (0.5 µM) or high concentrations of physostigmine (5 µM) have opposite effects, namely enhancement or depression of nicotine induced currents (0.1 mM, 20 ms), respectively. B: dose/response curves for nicotine as control (right) and in the presence of physostigmine (left; 0.5 µM; n=4–14 cells). The allosteric modulator action enhances all responses, including the maximal one. C: Histograms comparing the enhancing action of CGRP 1-6 (1 µM), physostigmine (0.5 µM) and their combined application. Note their resulting additive effect. The asterisks indicate significance level (n=5 cells). D: Histograms comparing the physostigmine depressing action (5 µM) on nicotine induced responses and the reversal of this block by the subsequent application of CGRP 1-6 (1 µM; n=4). In these graphs the nicotine response is expressed as ratio of currents in the presence of drug (I)/control solution ($I_{control}$).

EXAMPLE 1

Preparation of Chromaffin Cells

Cultures of rat chromaffin cells were prepared according to the Brandt method (Brandt et al., 1976, Giniatullin et al., 1999, Khirough et al., 1997, 1998). 25–35 day old rats were anaesthetized by increasing $CO_2$ levels and then their adrenal glands were removed. The medullary part was separated from the cortical portion of the gland in buffer solution (pH 7.2) containing (mM): NaCl 137, KCl 3, $Na_2HPO_4$ 0.7, HEPES 25, glucose 10 and 350 U ml$^{-1}$ of penicillin and streptomycin.

Cells were successively dissociated from fragments of medullary tissue at 37° C. over about 60 min, by passing them through a Pasteur pipette at 15 min intervals, and by enzymatic treatment with collagenase A and DNAse I (0.5 U ml$^{-1}$ and 10 µgml$^{-1}$). The cell containing suspension was then centrifuged at 700 rpm for 5 min and washed twice in HEPES buffered medium. The cells, after re-suspension in DMEM culture medium (Dulbecco's modified Eagle's medium) with addition of 10% FCS (calf fetal serum), were plated on poly-lysine (5 mg/ml)-pretreated Petri dishes and cultured at 37° C. for 1–2 days in 5% $CO_2$ containing atmosphere.

A set of experiments was carried out using 128 cells which represent myotubes and therefore contain muscle-type nicotinic receptors. For this purpose the cells were prepared according to method by Irintchev et al. (1997).

EXAMPLE 2

Patch-clamp Electrophysiological Records

Dishes containing cultured cells (used from 0 to 3 days after their preparation) were placed on an inverted Nikon DIAPHOT™ microscope and continuously superfused (5–10 ml/min) with control saline containing (mM): NaCl 135, KCl 5, MgCl2 1, CaCl2 2, glucose 15, HEPES 10 (pH 7.4 with addition of NaCH; 285 mOsm osmolarity). The patch pipettes, obtained from glass capillary tubes (1.5 mm o.d.) had 5–6 MΩ resistance when filled with intracellular solution containing: (mM) CsCl 120; HEPES 20; MgCl2 1; Mg2ATP3 3, BAPTA 10 (240 mOsm). The pH of the intracellular solution was adjusted to 7.2 with CsOH. Unless otherwise specified, all recordings were carried out at −70 mV membrane potential. After obtaining whole-cell configuration (Hamill et al. 1981), each cell was stabilized for 5 mm period, after which membrane ionic currents, mediated by nAChR activation, were recorded, filtered at 1 kHz, and stored in a PC for subsequent analysis with the pCLAMP 6.04 program (Axon Instruments Inc., Foster City, Calif.).

EXAMPLE 3

Administration of Substances nAChR agonists were administered to single cells by a pressure system from a micropipette containing a relatively concentrated solution and placed at 15-25 µM distance from the recorded cell. Preliminary tests indicated that, with this method, the concentration of a substance at the target cell membrane is 3 times lower than the one within the pipette (Giniatullin et al., 1996) and were confirmed by experimental and theoretical tests using as a reference rapid application by superfusion (Di Angelantonio and Nistri 2001). This method allows very rapid administration of a chemical substance with a few ms latency to observe a cell response. For application of antagonists, test compounds and control solution we used a rapid superfusion system (Bio-logic, France) consisting of an array of glass capillary tubes (0.8 mm o.d.) which, through rapid rotation, generate solution flow onto the treated cell. In this case the exchange time between two solutions is about 50 ms.

EXAMPLE 4

PCR from Single Cells

PCR is preceded by a reverse transcriptase reaction (RT). To this end the cytoplasm of cells (after electrophysiological recording) was withdrawn under visual control, using a 10 ml syringe connected to the recording pipette. Cytoplasm was added to the reverse transcriptase reaction mixture according to the methodology described by Jones et al. (1999). During this reaction, RNA contained in any cell is transformed into cDNA and stored at 4° C.

For PCR analysis we used the method described below. The first step for the DNA analysis is amplification (by means of a specifically prepared oligonucleotide mixture) of all sequences corresponding to nicotinic receptors (for a complete description of the PCR technique, see Maniatis et al., 1989). The volume of each reaction was sufficiently large to allow its subdivision required for amplification of the individual sequences corresponding to various receptors (Jones et al. 1999). After this pre-amplification, the reaction products were divided according to the individual amplification reactions, each one with its own specific primer (Jones et al. 1999).

For our experiments we amplified the following sub-units: α2, α3, α4, α5, α6, α7, β2, β3, β4. The PCR products were then analyzed by standard electrophoresis (Jones et al. 1999).

EXAMPLE 5

Synthesis of Peptide Fragments a. Assembly

Peptides were assembled according to the solid phase Fmoc synthesis strategy using t-butyl (for a detailed description of the technique, see Chan and White, 2000).

The starting resins were 1% DVB cross-linked Fmoc-Rinke-Amide-Aminomethyl PS or Fmoc-M-Wang PS.

The protection procedure was as follows:
1. DMF (3×30 sec)
2. 25% piperidine (3×3 min)
3. DMF (6×30 sec)
4. DMF coupling (1×15 min)
5. DMF coupling (1×15 min)
10 m/g of peptide resin was used at each step.

The amino acid coupling (five-fold excess) was carried out in DMF in the presence of BOP, Hobt and DIEA.

The following reagents were used for protection of the side chains.
  t-butyl for Serine or Threonine
  trityl for Asparagine or Cysteine b. Peptide Bond Cleavage Peptides were separated from the resin and their protection removed by trifluoro acetic acid.

First step:
  the resin-peptide conjugate was placed in TFA and stirred for 150 min in the presence of phenol, ethanedithiol, thioanisole and water as scavengers.

Second step:
  the solution was cooled and the peptide isolated by precipitation using methyl t-butyl ether and subsequent centrifugation.
  the crude peptide was then dissolved in a mixture of acetonitrile/water/acetic acid (70/30/1) and lyophilized.

Data Analysis

The data are reported as mean±standard deviation (n=cell number); the statistical significance was evaluated with the Wilcoxon test (for non-parametric data) or paired t-test (when data had Gaussian distribution). A difference was considered statistically significant when $p \leq 0.05$.

EXAMPLE 6

Study of the Effects of CGRP Peptide Muteins on the Response Mediated by the nAChR Activation A study carried out according the methodologies described in examples 1–5 has demonstrates the following aspects:
  Identification of the sub-units constituting nAChRs of rat chromaffin cells;
  CGRP 1-6 enhances nAChR mediated responses:
  Independence of the CGRP 1-6 effect from the membrane potential;
  Comparison between CGRP 1-6 and CGRP 1-7;
  Effect of fragments shorter than CGRP 1-6;
  Effect of the CGRP 1-7A fragment;
  Interaction amongst CGRP fragments and nAChR allosteric modulators
  Effect of CGRP 1-6 on muscle-type nicotinic receptors
  Sub-units Constituting nAChRs of Rat Chromaffin Cells As a first approach to the study of highly selective cholinergic substances, the heterogeneity of nAChRs requires describing the receptor types of chromaffin cells to identify pharmacological selectivity of novel compounds.

FIG. 2 shows the analysis of mRNA content in 15 chromaffin cells obtained with single cell RT-PCR. It is clear that rat chromaffin cells possess heteromeric nAChRs consisting of α3, α6, β2 and β4 sub-units. While α3β4 is the prevalent receptor assembly in ganglia of the autonomic nervous system, α6 and β2 are typical sub-units of the central nervous system and, in particular, they are the main sub-units of the cholinergic pathways included within the basal ganglia dopaminergic system (Ferrari et al. 1999, Le Novere et al. 1999, 1996, Charpantier et al. 1998). Furthermore, studies carried out on heterologous expression systems have shown that α6 can form functional receptors both with β2 and α3β4 subunits (Fucile et al. 1998). These results indicate that rat chromaffin cells are reliable models containing α3β4, α6β2, α6β4 and finally α3α6β4 type receptors.

Enhancement of nAChR Mediated Responses by CGRP 1-6

FIG. 3 shows data obtained applying a short nicotine pulse (the typical nAChR agonist; 0.1 mM within the pipette; variable length pulses as shown in FIG. 3) to a chromaffin cell. FIG. 3A demonstrates, in the presence of CGRP 1-6 (1 μM), the surprising enhancement of submaximal nicotinic responses induced, for example, by a 20 ms pulse application. On the contrary, on the same cell this enhancement was absent when the nicotine pulse was long (200 ms) enough to saturate nAChRs and generated a maximal current (FIG. 3B). The CGRP 1-6 effect was developed so rapidly that it was already observed after only 5 s application, and it was readily reversible after about 1 min wash (FIG. 3C). This phenomenon was not associated with any direct action by CGRP 1-6 on resting membrane conductance or baseline current. Thus, CGRP 1-6 was a modulator of nAChRs, but it did not act on the same in the absence of agonist.

In order to understand the pharmacological mechanism of action of this peptide fragment, it would be necessary to construct nicotine dose-response curves before and during CGRP 1-6 application. Because of the rapid nAChR desensitization, it is, however, very difficult to perform this type of experiment by applying a broad range of nicotine concentrations. To circumvent this technical problem, one can fill a glass pipette with a fixed nicotine concentration and apply it in various amounts by changing the duration of pressure pulses, kept always very short (tens of ms) to minimize desensitization (see Giniatullin et al. 1999; Di Angelantonio and Nistri 2001).

Using this method, the nicotine dose response curve for control conditions is shown in FIG. 3D (small squares). When the same nicotine pulses were applied in the presence of CGRP 1-6 (1 μM), the curve was shifted to the left in a parallel fashion without modification of the maximum response. The asterisks indicate that the enhanced responses were statistically different from correspondent controls. This parallel shift suggest that, on the basis of current knowledge about the behavior of membrane receptors (Colquhoun 1998), the site of action of CGRP 1-6 action was similar to the one of nicotine, and the interaction of these two substances with the receptor apparently depended on properties such as relative binding affinity and substance concentration.

It was recently demonstrated that some substances, classified as "allosteric potentiator ligands" (APL) (Maelicke and Albuquerque 2000), facilitate nAChR responses with distinct pharmacological properties including, for example, a very narrow concentration range to generate such an effect. On the contrary, CGRP 1-6 showed its nAChR enhancing action within a very broad concentration range: by testing 1,000 fold different concentrations (0.05–100 $\mu$M), we observed that the CGRP 1-6 enhancing action had a threshold value of 0.1 $\mu$M (105±7% potentiation, n=7) and that it grew significantly to a maximum value (156±6%, n=5) of 50 $\mu$M. This phenomenon is represented in FIG. 4A which shows the current response increase to a constant nicotine dose (20 ms; 0.1 mM) in the presence of increasing CGRP 1-6 concentrations. The CGRP 1-6 enhancing effect was exerted also when nAChRs were activated by cytisine (20 ms; 0.1 mM, FIG. 4B), confirming that this facilitation did not depend on the type of nicotinic agonist chosen. Acetylcholine was not tested because this substance is rapidly hydrolyzed by cholinesterases, making difficult to obtain reliable responses.

Independence of the CGRP 1-6 Effect From the Membrane Potential

The enhancing action of the peptide is independent from the membrane potential as indicated in FIG. 4C, which shows data from 6 cells whose membrane potential was set at −40, −70 and −100 mV. The degree of enhancement remained constant, indicating therefore that the sensitivity of the cells to the CGRP 1-6 action is not affected by the cell activity level.

Comparison Between CGRP 1-6 and CGRP 1-7

We examined whether the CGRP 1-6 enhancing ability could compete with the CGRP 1-7 induced inhibition. FIG. 4D shows that, while CGRP 1-6 enhancement was on average 31 % and CGRP 1-7 inhibition was 42%, the concurrent application of these two fragments (1 $\mu$M concentration of both) eliminated both effects and that there was not significant variation in nicotine currents (99±4%, n=6). This result suggests that both peptides act on the same receptor site although with opposite effects.

Effect of Fragments Shorter than CGRP 1-6

FIG. 5A shows that CGRP 1-5 can enhance nicotinic currents via a concentration dependent action. This action is smaller than the one by CGRP 1-6. In fact, while the CGRP 1-6 (1 $\mu$M) enhancement was 31±7% (n=6), to achieve a similar enhancement (26±4%; n=5) with CGRP 1-5 the concentration must be 10-fold higher (10 $\mu$M).

CGRP 1-4 (1 $\mu$M) retains a very small enhancing effect (8±1%; n=14) while CGRP 1-3 (1 $\mu$M) does not modify nicotine induced currents (0±1% n=7). These data are summarized in FIG. 5B which presents also the antagonism data for native CGRP and CGRP 1-7. These results indicate that a series of peptide fragments corresponding to the CGRP N-terminal chain can enhance nAChR activity at varying degree. This phenomenon should help future studies about the structure-activity relation of these peptides.

Effect of the CGRP 1-7A Fragment

In view of the enhancing action of the 1-6, 1-5 and 1-4 fragments which counteracts the inhibiting effect of the 1-7 fragment, we noted that the latter includes a disulfide bridge linking two cysteines (in positions 2 and 7). We considered that this disulfide bridge may represent the structure inhibiting nicotinic receptor activity and that this is missing from shorter fragments with enhancing action. To support this hypothesis we tested the effect of the 1-7A fragment in which cystein in 7 position was replaced by alanine. FIG. 6A shows that the fragment 1-7A enhanced (+18%) the current generated by a 20 ms nicotine pulse; this effect was reversible after an about 1 min wash. FIG. 6 indicates the time profile of the CGRP 1-7A action on the nicotine response: the enhancement developed rapidly and reached apparent equilibrium conditions (maximum enhancement=17±4%; n=8) and rapid recovery on washout. FIG. 6C reports nicotine dose/response curves in control solution (squares) or in the presence of 1 $\mu$M CGRP 1-7A. The curve was significantly shifted to left without increase in the maximum response (n=8 cells).

These experiments demonstrate that the CGRP 1-7A fragment, devoid of the cyclic structure imparted by the disulfide bridge, enhanced the nicotine action on the chromaffin cells.

Interaction Among CGRP Fragments and nAChR Allosteric Modulators

A comparison among CGRP fragments and APL acting substances is necessary to explore their potential synergy and to better understand the mechanism of action of CGRP fragments. Physostigmine (eserine), a cholinesterase inhibitor, is also known to possess an allosteric effect on nicotinic receptors, at doses lower than for cholinesterase inhibition (Maelicke et al., 1997, Maelicke and Albuquerque 2000). First, we verified if the action of physostigmine on chromaffin cell nAChRs corresponded to the one reported in the literature. To this end, nicotine was applied in the presence of low (0.5 $\mu$M) or high (5 $\mu$M) physostigmine concentrations. FIG. 7A shows that 0.5 $\mu$M physostigmine enhanced (on average 28±5%; n=14) and that 5 $\mu$M physostigmine depressed (on average 48±5%; n=4,) the response to nicotine (0.1 mM nicotine; 20 ms).

Previous studies (Maelicke et al. 1997) have suggested that the physostigmine concentration evoking the maximum enhancement is 0.5 $\mu$M. Further increases in concentration rapidly inhibit nAChRs. Our present experiments accord with these observations and confirm physostigmine to act on the chromaffin cells like an APL compound and thus different from CGRP 1-6. FIG. 7B shows the nicotine dose response curve in control solution and in the presence of 0.5 $\mu$M physostigmine: in the latter case the curve was shifted to left and displayed an increase in its maximum response. None of these properties was observed in the experiments carried out with CGRP 1-6 (see FIG. 3D).

FIG. 7C shows mean values of experiments when nicotine was applied in the presence of CGRP 1-6 (1 $\mu$M) or physostigmine (0.5 $\mu$M), after previous confirmation that each substance per se significantly enhanced nAChR responses. With combined application of the two modulators the enhancement was 37±6%, that is substantially near the sum of the two individual effects (21±4% and 10±1% for CGRP and physostigmine, respectively). On the contrary, application of a high dose (5 $\mu$M) of phystigmine caused 77±1% reduction in nicotine responses. In this case, concurrent application of CGRP 1-6 (1 $\mu$M) counteracted partially the physostigmine inhibition because nicotine currents corresponded to 79±1% of the control (n=4). These results clearly demonstrate separation between physostigmine and CGRP 1-6 effects and suggest that these molecules interacted with nAChRs differentially.

Study of the Effect of CGRP 1-6 on Muscle-type Nicotinic Receptors

The above described experiments demonstrated the interesting enhancing action of CGRP 1-6 but did not clarify its selectivity towards nAChRs. To this end we studied whether this peptide could affect nicotinic currents recorded from cultured muscle cells (myotubes, I28). These cells were kept at −60 mV potential by the patch electrode. Nicotine application (100 µM via the superfusing solution) induced mean responses of 1.06±0.22 nA amplitude (n=7), readily reversible after wash. This nicotine concentration corresponded to the one evoking half maximal responses. In the presence of 1 µM CGRP 1-6 (pre-applied for 2 minutes), the amplitude of nicotine responses did not change (1.09±0.24 nA corresponding to 101±2% of the controls; n=7). These observations confirm that the action of CGRP 1-6 on nAChRs was not extended to muscle-type nicotinic receptors.

REFERENCES

Amberla K, et al. (1993). *Acta Neurol Scand Suppl* 149: 55-7
Bartus R T, et al. (1982). *Science* 217: 408–14
Benwell M E, Balfour D J, Anderson J M (1986),. *Br J Pharmacol* 89:341–7.
Bertrand S, et al. (1998). *Br J Pharmacol* 125:751–760
Breese C R, et al. (1997). *J Pharmacol Exp Therapeu* 282:7–13
Changeux J P, Edelstein S J (1998). *Neuron* 21:959–80
Chan W C, White P D eds. (200) Fmoc Solid Phase Peptide Synthesis: A Practical Approach (Practical Approach Series). Paperback
Charpantier E, et al. (1998). *Neuroreport* 9: 3097–101
Clementi F, Adlkofer F (2000) Special issue "nicotinic neuronal receptors" *Eu J Pharmacol* 393
Colquhoun D (1998). *Br J Pharmacol* 125:924–947.
Coyle J T, Price D L, DeLong M R (1983). *Science* 219: 1184–90.
Dani J A, Heinemann S (1996). *Neuron* 16:905–8
Decker M W, et al. *J Pharmacol Exp Therap* 270:3119–28
Di Angelantonio S., Nistri A. (2001) *J Neurosci Meths,* in press.
Ferrari R et al. (1999). *Neurobiol. of Aging* 20:37–46
Freedman R, et al. (1997). *Proc Nat Acad Sci USA* 94:587–92
Freedman R et al. (1995). *Biol Psychiatry* 38:22–33
Fucile S, et al. (1998). *T Eu J Neurosci* 10:172–8
Giniatullin R et al. (1996). *Br J Pharmacol* 119:1045–53
Giniatullin R, et al. (1999). *J Neurosci* 19 2945–2953
Gotti C, Fornasari D, Clementi F (1997). *Prog Neurobiol* 53:199–237
Hamil O P, et al. (1981). *Pfluegers Arch* 391:85–100
Irintchev A, et al. (1997). *J Physiol* 500 775–785
Janson A M, Moller A (1993). *Neuroscience* 57:931–41
Jones S, Sudweeks S, Yakel J L (1999). TINS 22: 555–61
Kihara T, et al. (1998). *Brain Res* 792:331–4
Khiroug L, et al. (1997). *Br. J. Pharmacol* 122:1323–1332
Khiroug L. et al. (1998) *J Neurosci* 18:2458–2466
Krause R M, et al. (1998). *Mol Pharm* 53:283–294
Le Novere N, et al. (199). *Neuroreport* 10:2497–501
Le Novere N, Zoli M, Changeux J P (1996). *Eur J Neurosci* 8:2428–39
Levin E D, et al. (1992). *Behav Neu Biol* 58:152–8
Lindstrom J (1997). *Mol Neurobiol* 15:193–222
Lu B, Fu W M, Greengard P, Poo M M (1993). *Nature* 363:76–79
Maelicke A, Albuquerque E X (2000). *Eu J Pharmacol* 393:165–170
Maelicke A, et al. (1997). *J Recep Sig Ttransdu Res* 17:11–28
Maggio R, et al. (1998) *J Neurochem* 71:2439–46
Maltby N, et al. (1994). *BMJ* 308:879–83
Maniatis T, et. al. (1989) Molecular Cloning: A Laboratory Manual (3 Volume Set); Plastic Comb
Miles K, Greengard P, Huganir R L (1989). *Neuron* 2: 1517–1524
Morens D M, Grandinetti A, Reed D, et al. (1995). *Neurology* 45:1041–51
Mulle C, et al. (1988): *Proc Nat Acad Sci USA* 85:5728–5732
Nordberg A, et al. (1998). *Alzheimer Disease & Associated Disorders* 12:228–37
Nordberg A, Svensson A L (1999). Drug Safety 19:465–80
Olale F, et al. (1997) *J Pharmacol Exp Neurobiol* 283: 675–83
Paterson D, Nordberg A (2000) *Progr Neurobiol* 61:75–111
Perry E, et al. (2000) *Eu J Pharmacol* 393:215–222
Perry E K, et al. (1995) *Neurosci* 64:385–95
Picciotto M R, et al. (1995) *Nature* 374:65–7
Rusted J, Graupner L, O'Connel N, Nicholls C (1994) *Psychopharmacol* 115:547–9
Schneider J S, et al. (1998). *Movement Disorders* 13:637–42
Schneider J S, Van Velson M, Menzaghi F, Lloyd G K (1998). *Ann Neurol* 43:311–7
Sjoberg S L, et al. *Int J Geriatric Phsycopharmacol* 1:145–149
Steinlein O K, et al. (1995) *Nature Genetics* 11:201–3
Warpman U, Nordberg A (1995) *Neuroreport* 6:2419–23
Weiland S, et al. (1996) *FEBS Letters* 398:91–6
Whithehouse P J, Hedreen J C, White C L 3d, Price D L (1983) *Ann Neurol* 13:243–8
Wonnacott S (1997) *Trends in Neurosciences* 20:92–8

The invention claimed is:

1. An isolated peptide consisting of the amino acid residues 1–4 of SEQ ID No. 1 or the amino acid residues 1–5 of SEQ ID No. 1 or the amino acid residues 1–6 of SEQ ID No. 1 or the amino acid of SEQ ID No. 2.

2. A composition comprising at least one peptide according to claim 1 and one (or more) pharmaceutically acceptable adjuvants and excipients.

3. The composition according to claim 2 further comprising physostigmine.

* * * * *